United States Patent [19]

Ching

[11] 4,247,475

[45] Jan. 27, 1981

[54] CHLOROFORMATES OF CYANOACRYLATES

[75] Inventor: Ta-Yen Ching, Schenectady, N.Y.

[73] Assignee: General Electric Company, Schenectady, N.Y.

[21] Appl. No.: 131,157

[22] Filed: Mar. 17, 1980

[51] Int. Cl.³ .............................................. C07C 121/70
[52] U.S. Cl. ........................ 260/465 D; 260/45.85 A; 528/199
[58] Field of Search ..................... 260/465 D, 45.85 A

[56] References Cited

U.S. PATENT DOCUMENTS

| | | | |
|---|---|---|---|
| 3,644,466 | 2/1972 | Strobel et al. | 260/465 D |
| 4,203,919 | 5/1980 | Gruber et al. | 260/465 D |

*Primary Examiner*—Dolph H. Torrence
*Attorney, Agent, or Firm*—Joseph T. Cohen; James C. Davis, Jr.

[57] ABSTRACT

Certain cyanochloroformates are described which have utility for imparting UV stability to polycarbonate resins.

6 Claims, No Drawings

CHLOROFORMATES OF CYANOACRYLATES

This invention is concerned with novel compositions of matter comprising a certain class of cyanochloroformate acrylates (hereinafter identified as "acrylates"). More particularly, the invention is concerned with compositions of matter having the general formula

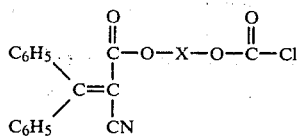   I.

where X is a divalent saturated alkylene group of the $C_{2-10}$ series. Among the divalent saturated alkylene groups which X can represent are, for instance.
—$CH_2CH_2$—, —$CH_2$—$(CH_2)_2$—$CH_2$—, —$CH_2$—$(CH_2)_4$—$CH_2$—, —$CH_2$—$C(CH_3)_2$—$CH_2$—, —$CH_2$—$(CH_2)_8$—$CH_2$—, etc.

These novel compositions can be used for end-capping polycarbonate resins (similarly as phenol is often used for the purpose), to markedly improve the UV stability of such resins over the use of other end-capped polycarbonate resins alone or when using other UV stabilizers admixed with the polycarbonate resin.

The acrylates (also identified as "chloroformates") of the present invention may be obtained by first effecting reaction between a compound of the formula

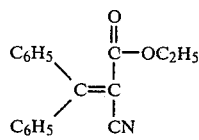   II.

and sodium methoxide in the presence of a dihydric alcohol of the formula

HO—X—OH   III.

where X has the meanings given above to give the compound of general formula

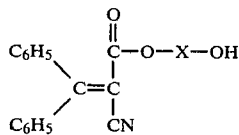   IV.

where X has the meanings above. Compounds of formulas II and IV and methods for preparing the same are found disclosed in U.S. Pat. Nos. 3,644,466 issued Feb. 22, 1972 and in 3,180,885 issued Apr. 27, 1965.

Thereafter, the compound of formula IV is treated in accordance with my invention with phosgene to form the compounds of formula I.

The use of the acrylates of formula I for end-capping polycarbonate resins to form UV-stable resins is more particularly disclosed and claimed in my copending application Ser. No. 131,156, filed concurrently herewith and assigned to the same assignee as the present invention, said application by reference being made a part of the instant application.

In order that those skilled in the art may better understand how the present invention may be practiced, the following examples are given by way of illustration and not by way of limitation.

EXAMPLE 1

This example illustrates the preparation of the chloroformate having the formula

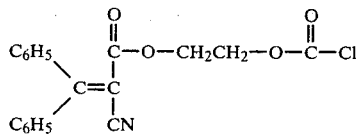   V.

More particularly, 0.35 mol of the cyanoacrylate of formula II, 1.0 mol ethylene glycol and a catalytic amount (about 0.1 gram) sodium methoxide was heated under reflux conditions in 200 ml of dry toluene for 30 minutes. After azeotropic removal of ethanol, the solution was washed with aqueous 5% HCl, then aqueous 5% sodium bicarbonate, and thereafter with water. The organic extract obtained was dried over magnesium sulfate after which the solvent was evaporated after first subjecting the dried organic extract to filtration. This resulted in quantitative yield of the compound having the formula

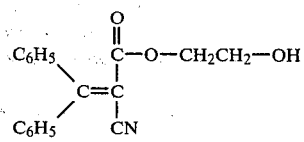   VI.

The identity of this compound was established by NMR, and by infrared analysis. The chloroformate of formula V was prepared by first forming a solution of 1 mol of phosgene and methylene chloride by bubbling the phosgene into the methylene chloride at 0° C. To this solution was added a methylene chloride solution containing 0.3 mol of the compound of formula VI dropwise while stirring. The solution thus obtained was warmed to room temperature gradually for 1 hour while continuing the stirring, and excess phosgene was then removed by purging nitrogen into the solution. Subsequent evaporation of the methylene chloride afforded quantitative formation of the chloroformate of formula V, as established by NMR and infrared analyses.

EXAMPLE 2

The chloro formate having the formula

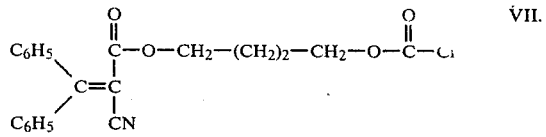   VII.

was prepared similarly as in Example 1 with the exception that 1,4-butanediol was used in place of the ethylene glycol of Example 1. Again, the identification of the chloroformate of formula VII was established by means of NMR and infrared analyses.

EXAMPLE 3

Employing the same conditions as was used in Example 1 but instead using neopentyl glycol in place of the ethylene glycol, the compound having the formula

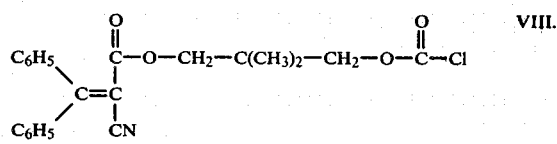
VIII.

was obtained. Identification of this chloroformate was established by NMR and infrared analyses. The immediate precursor of this compound had a melting point of 67°–69° C.

EXAMPLE 4

The compound having the formula

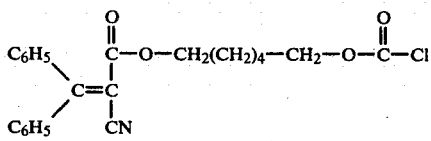
IX.

was prepared similarly as in Example 1 with the exception that 1,6-hexanediol was used in place of ethylene glycol. The identity of the compound of formula IX was established by means of NMR and infrared analyses.

All the chloroformates of Examples 1 to 4 were viscous liquids.

EXAMPLE 5

The chloroformate of formula V was used to chain-stop a polycarbonate resin in the following manner. The chloroformate was added to Bisphenol-A and sodium hydroxide in the presence of a tertiary amine in the manner normally used to make polycarbonate resins (see U.S. Pat. No. 4,180,651—Mark issued Dec. 25, 1979, and assigned to the same assignee as the present invention). Phosgene was then bubbled through the mixture which was dissolved in methylene chloride until complete carbonation had been obtained to give a homopolymeric polycarbonate resin composed of recurring units of the formula

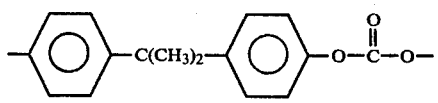
X.

where the end groups on the polycarbonate chain comprised the grouping

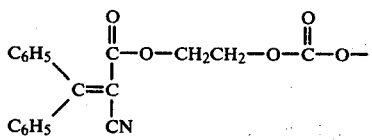
XI.

Comparison of the UV stability of this particular end-stopped polycarbonate resin with a polycarbonate resin end-capped with the usual end capping compound, namely, phenol and a similar polycarbonate resin end-capped with phenol, but additionally containing 0.3 weight percent of a well known UV stabilizer (Cyasorb 5411) showed that the polycarbonate end-stopped with the chloroformate of formula IV had much better resistance to UV light by a factor of 3 to 4, after three weeks, than the other two polycarbonate resin compositions.

What I claim as new and desire to secure by Letters Patent of the United States is:

1. A composition of matter having the general formula

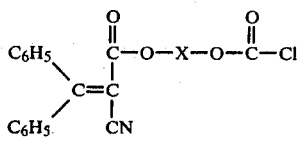

where X is a divalent saturated alkylene group of the $C_{2-10}$ series.

2. A composition of matter having the formula

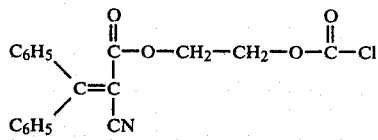

3. A composition of matter having the formula

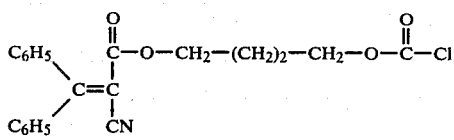

4. A composition of matter having the formula

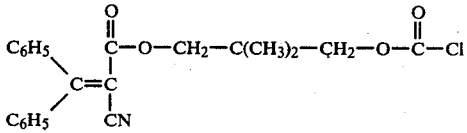

5. A composition of matter having the formula

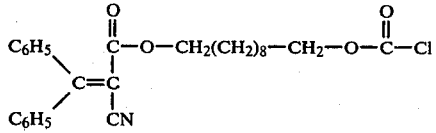

6. A composition of matter having the formula

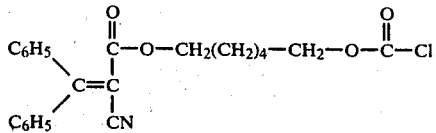

* * * * *